United States Patent [19]

Lazarre

[11] Patent Number: 4,671,099
[45] Date of Patent: Jun. 9, 1987

[54] DEVICE FOR MEASURING THE THERMODYNAMIC CHARACTERISTICS OF A FLUID

[75] Inventor: Flavien Lazarre, Pau, France

[73] Assignee: Societe National ELF Aquitaine (Production), Courbevoie, France

[21] Appl. No.: 894,708

[22] Filed: Aug. 8, 1986

Related U.S. Application Data

[63] Continuation of Ser. No. 487,874, Apr. 22, 1983, abandoned.

[30] Foreign Application Priority Data

Apr. 26, 1982 [FR] France .............................. 82 07121

[51] Int. Cl.⁴ .............................................. G01N 9/00
[52] U.S. Cl. ........................................ 73/30; 73/32 A
[58] Field of Search ...................... 374/16, 22, 27, 30, 374/32 A, 10, 11, 14, 54

[56] References Cited

U.S. PATENT DOCUMENTS

| 2,943,476 | 7/1960 | Bernstein | 73/32 A |
| 3,462,997 | 8/1969 | Roach et al. | 374/54 X |
| 3,729,981 | 5/1973 | Grady et al. | 374/54 |
| 4,170,128 | 10/1979 | Kratky et al. | 73/30 R |
| 4,295,368 | 10/1981 | Jannone | 374/54 |
| 4,297,872 | 11/1981 | Ikeda et al. | 73/32 A |
| 4,348,117 | 9/1982 | Michels | 374/27 X |
| 4,349,881 | 9/1982 | November et al. | 73/32 A X |
| 4,357,824 | 11/1982 | Foss et al. | 374/54 X |
| 4,428,684 | 1/1984 | Kuraoka | 374/157 X |

FOREIGN PATENT DOCUMENTS 2229056 6/1974 France .

Primary Examiner—Daniel M. Yasich
Attorney, Agent, or Firm—Brisebois & Kruger

[57] ABSTRACT

An enclosure 1 has a measurably variable volume chamber 2, a control for controlling the temperature of the fluid contained therein and apparatus for measuring the pressure of the fluid. The chamber is selectively connectable, on the one hand, to a filling device 6, for introducing the sample, and on the other hand to a fluid extraction apparatus 7, 8. The enclosure 1 is selectively connectable to a tubular loop 9 having a circulation pump 10 and apparatus 11 for measuring the density of the sample of circulating fluid. By varying the volume of chamber 2, the thermodynamic characteristics of monophase and diphase fluids can be accurately determined. The apparatus is especially useful for the study of fluid of hydrocarbon deposits.

6 Claims, 6 Drawing Figures

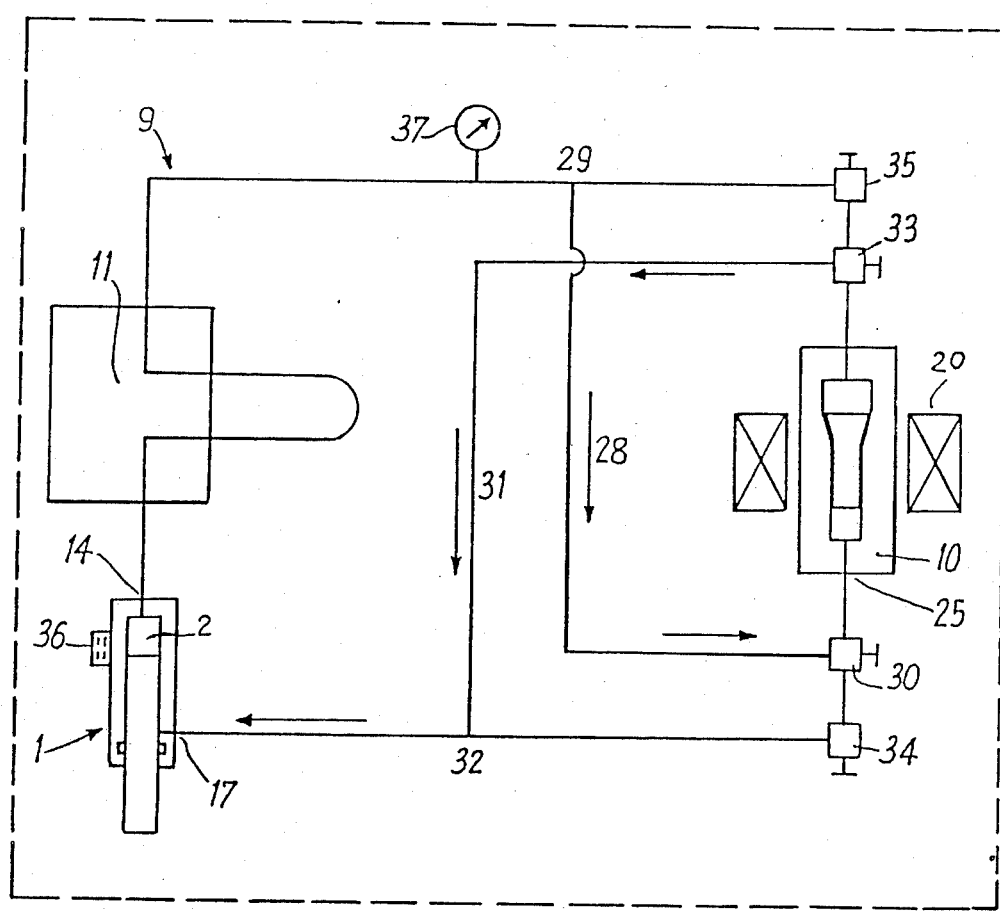
Fig:6

DEVICE FOR MEASURING THE THERMODYNAMIC CHARACTERISTICS OF A FLUID

This is a continuation of application Ser. No. 487,874 filed Apr. 22, 1983 and now abandoned.

BACKGROUND OF THE INVENTION

The present invention relates to apparatus for measuring the thermodynamic characteristics of a fluid, particularly the density of the fluid.

The pressure P, the specific volume or density Vs, and the temperature T of a test sample are related by the function:

$$f(P, V_s, T) = 0$$

the knowledge of which is indispensible for rational programs for exploiting hydrocarbon deposits, and also for the construction and management of surface processing facilities of these hydrocarbons. In general, the knowledge of the equation of the state of a fluid constitutes the first stage of any study for the industrial utilization of the fluid.

DESCRIPTION OF THE PRIOR ART

It is known per se to construct a curve system defining Vs and P for different temperatures with devices or apparatus comprising essentially an enclosure provided with means for measurably varying its volume, means for controlling the temperature of the fluid contained therein while maintaining it constant and for measuring, the pressure, and means for measuring the density of the fluid discontinuously by weighing. Such an enclosure is removably connected, on the one hand, to a device for filing the enclosure with the test fluid and on the other hand, to a fluid extraction or evacuating device for removing the fluid after testing.

The variation of volume of the enclosure, or the volume available for the fluid, is obtained either by displacement of mercury by means of a piston pump, or by displacement of a piston in the enclosure itself constituted by a cylinder. These different devices have the same defect: being practically static, they require the use of means of processes for homogenizing the fluid, thus complicating the apparatus and considerably increasing the duration of a test, and thus risking inaccuracy and error.

FIELD OF THE INVENTION

The apparatus according to the invention allows this difficulty to be overcome by permitting the measurement of the density and the pressure of small volumes of fluid during circulation in a tubular loop, according to a dynamic process guaranteeing homogeneity or uniformity of the sample, in the case of a monophasic fluid, maintaining the thermodynamic balance when the sample is polyphasic, and in both cases, with considerably reduced measurement times.

SUMMARY OF THE INVENTION

The known apparatus for measuring thermodynamic characteristics, such as density, of a fluid sample comprise an enclosure provided with means for measurably varying the volume, means for controlling the temperature of the fluid contained in the enclosure, and means for measuring the pressure. A connection arrangement is provided for connecting and disconnecting the enclosure to a filling device and to introduce the sample to a fluid extraction device to remove the sample after the test. Apparatus according to the invention is characterized in that enclosure is connected to a tubular loop comprising a circulation pump and apparatus for measuring the density of the circulating fluid sample.

In certain embodiments, the enclosure has a variable volume and is connected to the tubular loop through a single inlet or orifice at a time.

Generally, the variable volume enclosure is connected to the tubular loop by a valve either to a high orifice communicating with the top of the enclosure, or to allow a low orifice communicating with the bottom of the enclosure.

These arrangements have been especially designed with a view to simulate the depletion of deposits, especially condensate gas pools, in order to test the different procedures to obtain optimal recovery.

In embodiments in which it is required to establish a circulation through the enclosure, to obtain homogenization of the sample fluid of constant mass, the variable volume enclosure is connected to the tubular loop, so that it is parallel with the apparatus for measuring the density, and by-passes it.

This parallel positioning is obtained by valves operable to selectively connect the suction of the circulation pump either with the high orifice, or with the low orifice of the enclosure.

This parallel positioning is obtained by valves operable to selectively connect the suction of the circulation pump either with the high orifice, or with the low orifice of the enclosure.

In the layout that allows the widest variety of tests, the variable volume enclosure is connectable to the tubular loop by both orifices, so the enclosure can be connected in series both with the circulation pump and with the apparatus for measuring the density, and can be connected to by-pass them.

According to certain embodiments, the two orifices of the enclosure are connected to the tubular loop, each by a flexible duct or hose allowing the enclosure to be displaced or inverted from one position in which the orifice that is connected to the suction side of the circulation pump is located in a low position with respect to the chamber of the enclosure, to a position in which the same orifice of the enclosure is located in a high position with respect to the chamber of the enclosure.

According to a preferred embodiment, the enclosure is connected to the tubular loop by both orifices, i.e. a first or high orifice of the enclosure and a second or low orifice of the enclosure.

A currently used apparatus to reverse the circulation of the fluid in the tubular loop is one in which the suction and discharge of the circulation pump are connected to the high and low orifices of the enclosure by valves operable to a first position in which the suction of the pump is connected to the high orifice of the enclosure and a second position in which the suction of the pump is connected to the low orifice of the enclosure.

In different embodiments, a magnetic pump is generally used as the circulation pump and a "diapson" device, i.e. a vibrating U-shaped tuning fork like tube, is used for measuring the density of the fluid in circulation.

In certain embodiments, the apparatus for measuring the density is tubular having a magneto-striction actuator and is provided with an inductor winding and a detector winding arranged coaxially of the tube.

BRIEF DESCRIPTION OF THE DRAWINGS

The invention will be better understood from reading the following description, given by way of nonlimiting examples, of embodiments illustrated in the drawings:

FIG. 6 shows the apparatus of FIG. 5 with flow in another direction.

DETAILED DESCRIPTION

Figure 1:
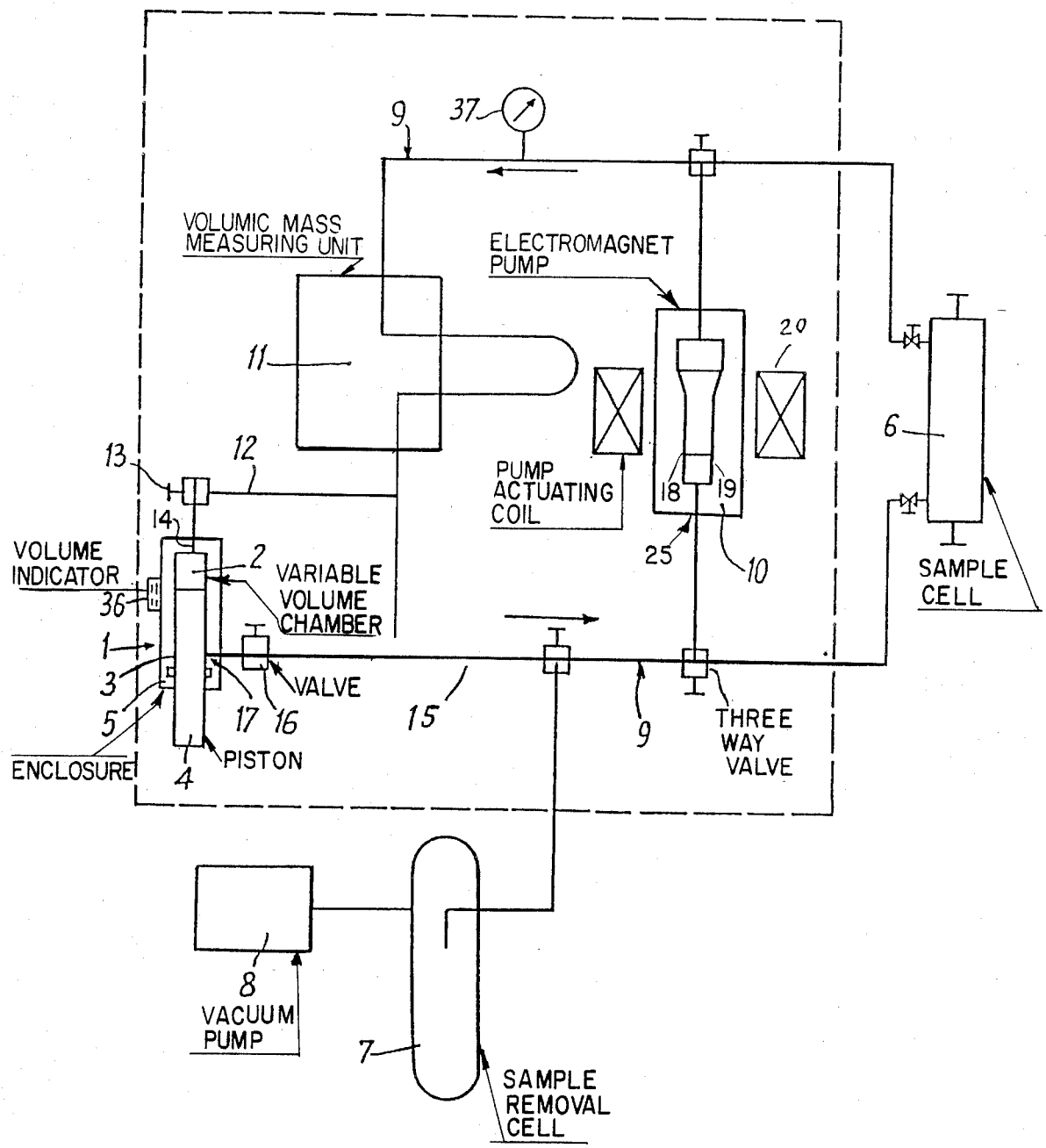
FIG. 1 shows apparatus according to the invention in which an enclosure is connectable to a tubular loop by either a high orifice, or low orifice of the enclosure.

FIG. 1 schematically shows a variable capacity chamber 2 in an enclosure 1 having a cylinder 3 in which is displaced a cylindrical piston 4 having a diameter slightly smaller than the internal diameter of the cylinder 3, the sealing between the cylinder 3 and the piston 4 being ensured by an annular device 5 known per se.

This enclosure 1 is selectively connectable, on the one hand, to a supply or filling device shown as a fluid transfer cell 6, and on the other hand, to an extraction device shown as a recovery cell 7 and an associated vacuum pump 8.

The selective connection for cells 6 and 7 is obtained by using three way valves, conventionally indicated on each of the branches or lines.

The enclosure 1 is, furthermore, connected to a tubular loop 9 comprising a circulation pump 10 and a device 11 for measuring the density of the fluid in circulation.

Communication between enclosure 1 and the tubular loop 9 is through a conduit 12 provided with a valve 13 connected to a high orifice 14 communicating with an upper portion of enclosure 1, or through a conduit 15 provided with a valve 16 and connected to a low orifice 17 communicating with a lower portion of enclosure 1.

FIG. 1 (like FIGS. 2, 3, 4, 5 and 6) schematically shows the pump 10 as a magnetic type of known pump in which a piston 18 is displaced in a cylinder 19 under the effect of the alternations of a magnetic field induced by a coil 20.

FIG. 1 (like FIGS. 2, 3, 4, 5 and 6) shows the device 11 for measuring the density of the fluid in circulation in loop 9 as a "diapson", i.e. a vibrating U-shaped tuning fork like tube such as that described in French Patent Publication No. 2,229,056 (application Ser. No. 74.881 of Mar. 15, 1974.) As described in French Publication No. 2,229,056, this "diapson" is a vibratable U-shaped tube, somewhat like a tuning fork, and the density of the fluid is measured by determining the characteristic frequency of vibration of the U-tube containing the fluid.

The U-tube is located in an enclosure or jacket of device 11, around which a fluid can flow to control the temperature of the U-tube and the sample fluid tube.

Of course, other means of measuring the density during circulation can be used, such as a known magnetostriction device in which the tube has a diameter that varies according to the frequency of the current of an induction coil. When the density of the circulating fluid varies, it is necessary to vary the frequency in order to relocate resonance. The density of the fluid is a function of the variation of frequency, according to a law, the coefficients of which are determined by calibration.

The arrangement shown at FIG. 1 allows connecting enclosure 1 with tubular circuit 9 either from the high orifice 14 of the enclosure, or from the low orifice 17, thus allowing, in the presence of a sample in a diphasic state, to circulate either a gaseous or a liquid phase in loop 9.

In FIG. 1, the circulation in loop 9 is an anti-clockwise direction and is indicated by the arrows, in FIG. 1.

The sample on which the test is performed is introduced under the conditions of the deposits, into the chamber 2, and the depletion of the deposit is simulated in a certain number of steps, for each of which a measurement of the density of the sample is taken by using the measurement loop. At each step, in order to take the measurement on the gaseous phase, the condensate is blown out by means of the recovery cell 7 so that the overall mass of the sample is reduced discontinuously throughout the test.

Figure 2:
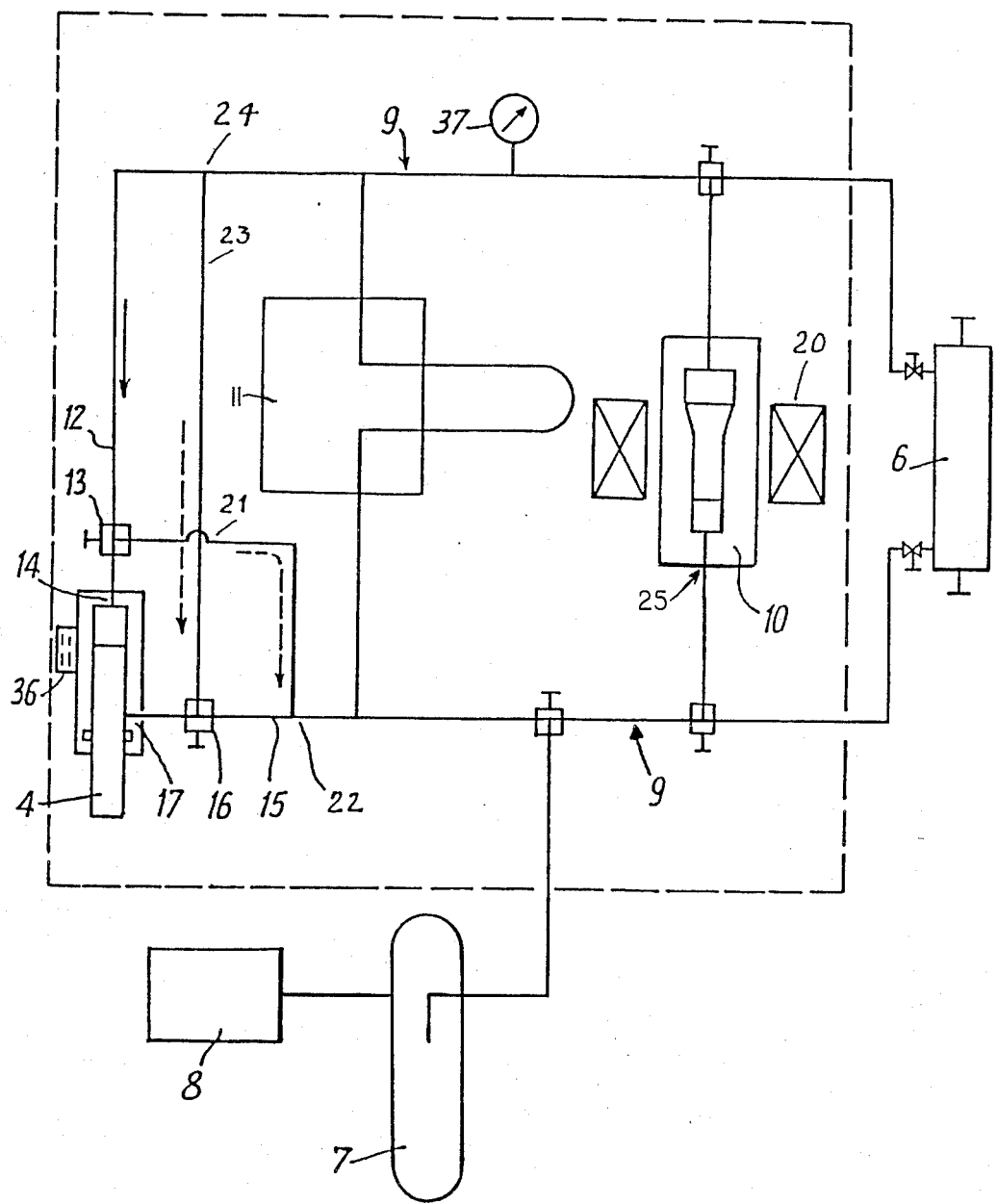
FIG. 2 shows an arrangement for connecting the enclosure to a tubular loop in parallel with a circulation pump, according to another embodiment of the invention.

FIG. 2 shows enclosure 1 connected to the tubular loop 9 and selectively connectable to the filling device 6 and to extraction device 7 and 8. Tubular loop 9 again comprises a circulation pump 10 and density measuring apparatus 11.

In FIG. 2, enclosure 1 is connected to tubular loop 9, so that it is in parallel with both circulation pump 10 and apparatus 11 for measuring the density, through a conduit 12 connected to high orifice 14 of enclosure 1 and a conduit 15 connected to low orifice 17 of enclosure 1.

Conduits 12 and 15 are provided with three way valves. Valve 13 is connected by a conduit 21 to a point 22 of the conduit 15 situated between valve 16 and loop 9. Valve 16 is connected by conduit 23 to a point 24 of conduit 12 between valve 13 and loop 9. The conduits 21 and 23 and the respective valves 13 and 16 constitute the communication means that allow connecting the intake of pump 10 with either high orifice 14 or low orifice 17 of enclosure 1.

Figure 3:
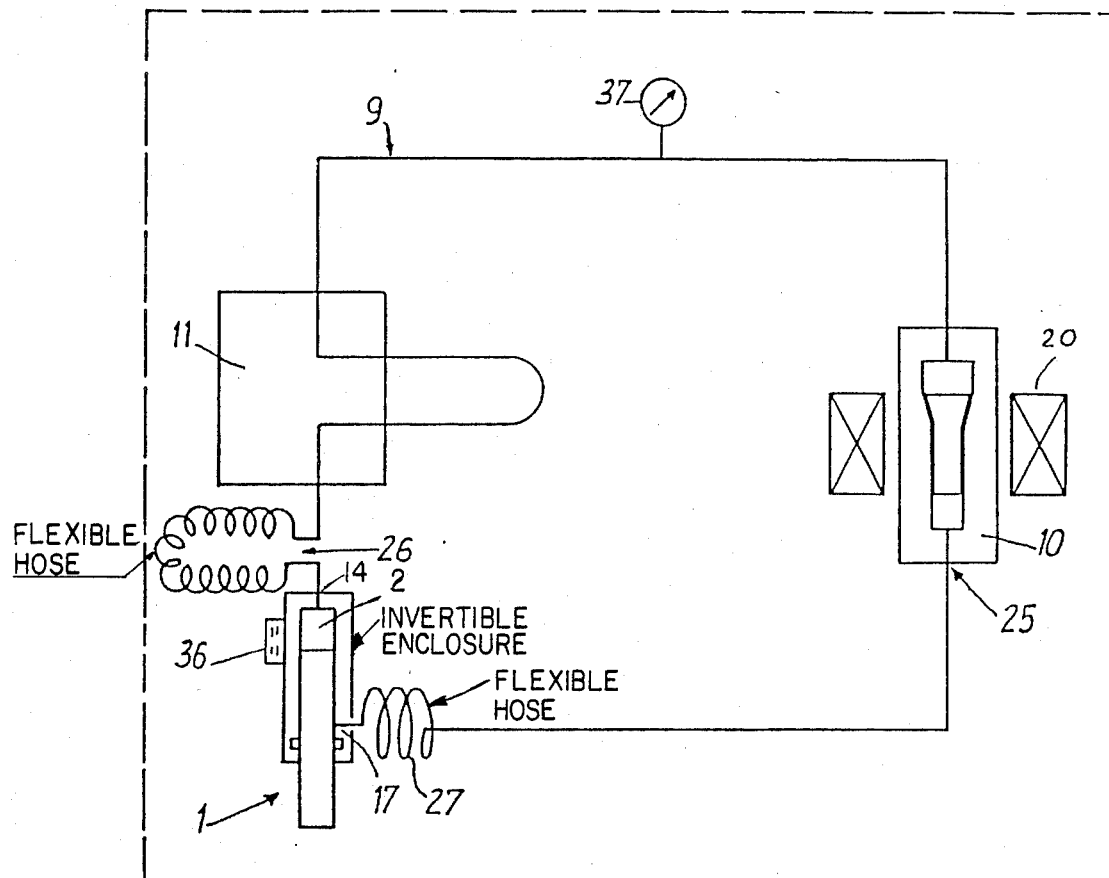
FIG. 3 shows an arrangement in which the enclosure is connected to a tubular loop in series with both the circulation pump and the density measuring apparatus by flexbile conduits or hoses.

FIG. 3 shows an arrangement in which enclosure 1 is connected to tubular loop 9 through two distinct orifices 14 and 17, enclosure 1 being coupled in series with both circulation pump 10 and apparatus 11 for measuring the density of the fluid sample in circulation in the loop.

Figure 4:
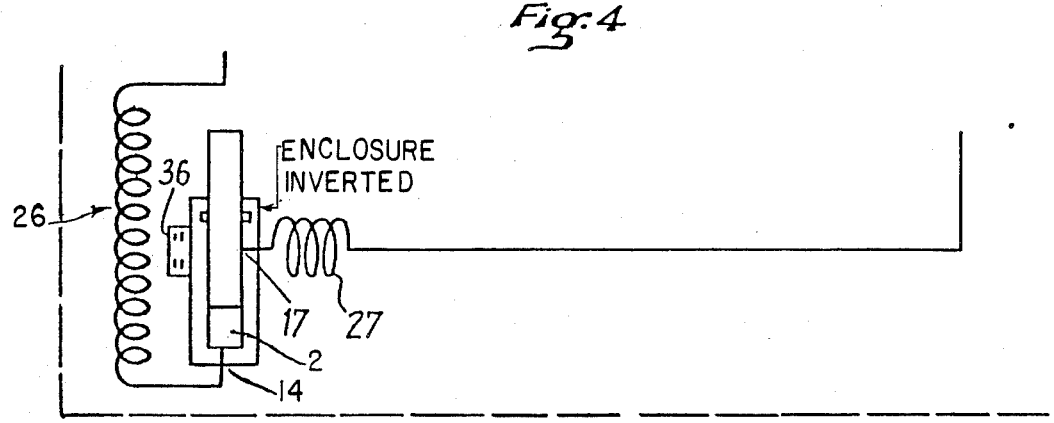
FIG. 4 shows the embodiment of FIG. 3 with the enclosure inverted to reverse the enclosure orifices.

Orifices 14 and 17 are connected to tubular loop 9 by ducts or hoses 26 and 27 allowing the displacement of enclosure 1 so that orifice 17 which is directly connected to the intake 25 of pump 10 can either be the low orifice (FIG. 3), or the high orifice (FIG. 4).

Figure 5:
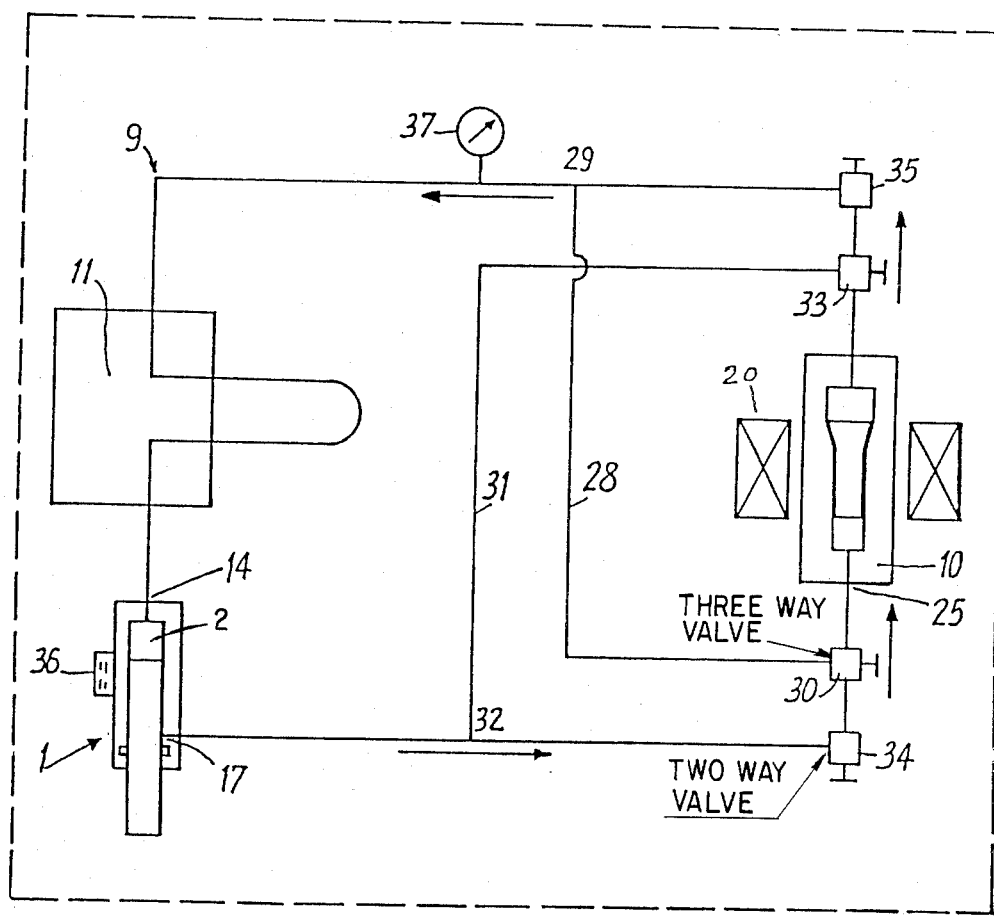
FIG. 5 shows apparatus in which enclosure is connected to a tubular loop in series with both the circulation pump and the density measuring apparatus, and showing flow in one direction.

FIGS. 5 and 6 show arrangements in which, as with FIG. 3, enclosure 1 is in series with both the circulation pump 10 and density measuring apparatus 11.

Valves provide for connection of intake 25 of circulation pump 10 either to high orifice 14 or low orifice 17 of enclosure 1.

This arrangement comprises a conduit 28 with one end connected to a point 29 of the tubular loop located between the discharge end of the pump 10 and the density measuring apparatus 11, and its other end connected to a three way valve 30 located immediately before intake 25 of the pump 10. A conduit 31 connects a point 32 of the tubular loop located between the density measuring apparatus 11 and the intake 25 of the pump 10, to a three way valve 33 located immediately beyond the output of the pump 10. Furthermore, a two way valve 34 is located between the point 32 and the three way valve 30 and a two way valve 35 is located between point 29 and the three way valve 33.

As shown at FIG. 5, with valves 34, 30, 33 and 35 open circulation of the fluid occurs according to the arrows from the low orifice 17 of the variable volume enclosure, and returns to the high orifice 14. If the fluid is in the diphasic state, it is the liquid phase that will be drawn from low orifice 17 and circulate and the density measuring device 11 will measure the density of the liquid phase.

As shown at FIG. 6, with valves 34 and 35 closed and valves 30 and 33 set to establish communication between the tubular loop and the respective conduits 28 and 31, there is circulation of fluid through the density measuring apparatus from the high orifice 14 which returns to low orifice 17 of enclosure 1. If the fluid is in the diphasic state, it is the density of the gaseous phase which will be measured.

The different figures show a device 36, of a type known per se, for measuring the volume available to the sample and for the display of this measurement, connected to the enclosure 1 and an indicator 37 of the pressure prevailing in the loop 9 is mounted on a compulsory passage portion of this loop.

OPERATION OF THE MEASURING DEVICE

In a standard manner, enclosure 1 and circulation pump 10 are maintained at a temperature T controlled by usual means known per se. The u-tube of apparatus 11 is normally maintained at the same temperature T either through the use of corresponding control means, or because the fluid that circulates is at this temperature T. The electronic device for measuring the density from the vibration characteristics of the apparatus 11 is maintained at a temperature compatible with its correct functioning, generally close to a constant standard temperature.

When a condensate gas is studied and T is close to dew temperature, it is possible to cool slightly the U-tube to $T-\epsilon$, in which $\epsilon$ represents some tenths of a temperature degree. This simple difference causes the condensation of dew on the internal wall of the U-tube, and varies the vibrating mass, thus causing a sharp and significant variation of the signal.

Under initial conditions, the initial volume of the fluid, presumed to be monophasic is $V_1$, the pressure is $P_1$ and the density is $m_1 = g/V_1$ in which g is the mass of fluid. The density $m_1$ is determined by apparatus 11, $V_1$ and g being initially unknown.

At constant temperature T, for a variation of volume $\Delta V_1$, $P_2$ is measured and $m_2$ is obtained from apparatus 11:

It is known that:

$$m_2 = \frac{g}{V_2} \text{ and } m_1 = \frac{g}{V_1}$$

Then: $V_2 \cdot m_2 = V_1 \cdot m_1 = g$ $\Delta V_1 = V_2 - V_1$; and $V_2 = \Delta V_1 + V_1$ $V_2 \cdot m_2 = (\Delta V_1 + V_1) m_2 - V_1 \cdot m_2$ $V_1 \cdot m_1 - V_1 \cdot m_2 = \Delta V_1 \cdot m_2$ $$V_1 = \frac{\Delta V_1 \cdot m_2}{m_1 - m_2} \tag{a}$$

$V_1$ being calculated from (a) g can be determined.

It can be seen that from the measurement of the different densities m, and the different, but known changes in volume $\Delta V$, it is possible to calculate the compressibilities or values of factor Z of the monophasic fluid, by the known non-ideal gas formula $PV = ZRT$, since the total volume Vn for a constant mass of the fluid is known from:

$$Vn = V_1 + \Sigma \Delta V$$

When a diphasic field is involved, it is possible to cause to circulate in the density measuring apparatus successively, each of the phases, provided a manifold of adapted valves is available. If m is the liquid density and $\mu$ the gaseous density, v the liquid volume and w the gaseous volume, then:

$$m \cdot v + \mu \cdot w = g \text{ (known) and } w = \frac{g - mv}{\mu};$$

$$v + w = Vn = V_1 + \Sigma \Delta V \text{ (known)}$$

$$v + \frac{g - mv}{\mu} = Vn = \frac{v \cdot \mu + g - m \cdot v}{\mu}$$

$$v(\mu - m) = Vn \cdot \mu - g$$

$$v = \frac{Vn \cdot \mu - g}{m - \mu} \text{ or } \frac{g - \mu \cdot Vn}{m - \mu}$$

The process thus provides f (P, V, T)=0 from measurements of the variation of the volume without knowing either the volume or the initial mass of the fluid, with only very small quantities of fluid (several cm$^3$ fill the density measuring apparatus, the circulation pump, the pipe lines and valves, and the volume varying apparatus, i.e. enclosure 1, can have a volume which is practically zero at the beginning of the test).

Furthermore, it is not necessary, in this part of the PVT measurement at least, to use mercury, the variations of volume being caused by a solid piston directly acting on the fluid.

The very small masses of the apparatus including the enclosure and the small amount of fluid required for a test lead to a low thermal inertia of the assembly, allow the test to be considerably accelerated, without incidence on the precision, particularly since the circulation pump ensures excellent mixing of the phase(s).

I claim:

1. Apparatus for measuring thermodynamic characteristics of a sample fluid comprising a tubular loop including a circulating pump having an intake fluid density measuring apparatus for measuring the density of a sample fluid as it is circulated through the density measuring apparatus by the circulating pump, an enclosure, a variable volume chamber in the enclosure, said chamber having a high orifice communicating with a top portion of the chamber, and a low orifice, means for measurably varying the volume of said chamber, communicating with a bottom portion of the chamber, means for selectively connecting the high orifice and the low orifice to said loop to selectively introduce fluid from the chamber into the loop from either orifice and to communicate to the loop changes in volume of the enclosure, means for introducing a sample fluid into the apparatus, and means for extracting the sample from the apparatus.

2. Apparatus according to claim 1, wherein the variable volume chamber is connected to the tubular loop to by-pass the circulating pump.

3. Apparatus according to claim 4 wherein said variable volume enclosure is connected in series in said tubular loop.

4. Apparatus according to claim 3 wherein said variable volume enclosure is invertible to change said high orifice to a low orifice and to change said low orifice to a high orifice.

5. Apparatus according to claim 1 wherein said pump has an intake, and the means for selectively connecting the variable volume chamber to the tubular loop comprises means for connecting either orifice of the chamber to the intake of the pump.

6. Apparatus according to claim 1 wherein the variable volume chamber is connected to the tubular loop to bypass the density measuring apparatus.

* * * * *